United States Patent
Mitchell (10) Patent No.: US 7,267,657 B1
(45) Date of Patent: Sep. 11, 2007

(54) SYSTEM AND METHOD FOR CORRECTING CLUB FOOT PROBLEMS IN CHILDREN

(76) Inventor: John R. Mitchell, 3041 Kiwi Ave., Washington, IA (US) 52353

( * ) Notice: Subject to any disclaimer, the term of this patent is extended or adjusted under 35 U.S.C. 154(b) by 250 days.

(21) Appl. No.: 10/708,808

(22) Filed: Mar. 26, 2004

(51) Int. Cl.
*A61F 5/00* (2006.01)

(52) U.S. Cl. .......................................... 602/29; 602/23

(58) Field of Classification Search ............... 602/5, 602/12, 23, 29, 28, 65, 27, 16; 128/882; 36/140, 142
See application file for complete search history.

(56) References Cited

U.S. PATENT DOCUMENTS

| | | | | |
|---|---|---|---|---|
| 2,585,342 A * | 2/1952 | Morgan | ........................ | 602/29 |
| 2,906,261 A * | 9/1959 | Craig | ........................ | 602/24 |
| 3,171,407 A * | 3/1965 | Rogers | ........................ | 602/24 |
| 3,523,526 A * | 8/1970 | Phelps | ........................ | 602/29 |
| 4,088,129 A * | 5/1978 | DiGiulio | ........................ | 602/23 |
| 4,249,523 A * | 2/1981 | Bidwell | ........................ | 602/24 |
| 4,495,943 A * | 1/1985 | Kurtz et al. | ........................ | 602/24 |
| 5,346,463 A * | 9/1994 | Devens | ........................ | 602/23 |
| 5,382,225 A * | 1/1995 | Sutcliffe | ........................ | 602/24 |
| 5,401,235 A * | 3/1995 | Devens | ........................ | 602/23 |
| 5,470,310 A * | 11/1995 | Sutcliffe | ........................ | 602/24 |
| 5,483,757 A * | 1/1996 | Frykberg | ........................ | 36/101 |
| 5,489,258 A * | 2/1996 | Wohnsen et al. | ........................ | 602/5 |
| 6,094,844 A * | 8/2000 | Potts | ........................ | 36/136 |
| 6,173,511 B1* | 1/2001 | Perrault | ........................ | 36/140 |
| 6,328,707 B1* | 12/2001 | Lampkins | ........................ | 602/23 |
| 2004/0244221 A1* | 12/2004 | Hall et al. | ........................ | 36/10 |

OTHER PUBLICATIONS

See the "Background of Invention" section on pp. 1-2 in the specification of this patent application.
A web page showing an article from the Department of Mechanical Engineering at the University of Michigan entitled "Design Expo: Fall 2002" regarding the Dennis Browne Splint.
Two Web pages of Markell showing the Tarso Open Toe Boots and Dennis Browne Splints.
Applicant admitted prior art.

* cited by examiner

*Primary Examiner*—Justine R. Yu
*Assistant Examiner*—Adam Brandt
(74) *Attorney, Agent, or Firm*—Simmons, Perrine, Albright & Ellwood, PL (57) ABSTRACT

A system and method for comfortably restraining a child's feet undergoing the Ponseti method for treatment of club feet, using a foot and ankle abduction orthosis, where the improvement includes a shoe with an integral sole and attachment mechanism, as well as having a soft pliable area around the feet and ankle support.

6 Claims, 8 Drawing Sheets

SYSTEM AND METHOD FOR CORRECTING CLUB FOOT PROBLEMS IN CHILDREN

BACKGROUND OF INVENTION

For years, the Dr. Ignacio Ponseti, a world-renowned expert in the treatment and management of club feet, has advocated use of a foot and ankle abduction orthosis (AFO) to prevent relapses of the deformity after the club-foot is corrected. Such a device consists of a bar of about the length between the baby's shoulders with high top open-toed shoes attached at the end of a bar in about 70 degrees of outward rotation. The splint is worn full time for two to three months, and thereafter at night and naps for 2 to 4 years. Corrective adjustments to the foot alignment are often necessary.

For many years, Dr. Ponseti used, with great success, the well-designed round-heeled high-top commercial shoes made by Penney's with soft leather. These are no longer available, and companies supplying much of the industry today don't produce adequate shoes attached to the bar. They often cause pressure sores and blisters on the baby's tender feet. Short and chubby clubfeet, even when well corrected, slip inside the shoe and even out of it, causing sores, loss of correction, great discomfort to the child and anguish to the parents.

Another problem is that it is often difficult to properly put the shoes on the patient's feet. In some instances, parents try to put the child's feet in the shoes while the shoes remain attached to the Dennis Browne splint. It is not only difficult for the parent, but uncomfortable for the child. Others have proposed shoes which have a simple latch mechanism which is attached to the sole of a shoe. Such a combination allows the parent to put the shoes on the child first and then latch the shoes to the Dennis Brown splint. These mechanisms attached to the bottom of the shoe are not only unsightly, but they are clumsy for the child to handle.

Consequently, there is an urgent need for improved methods and systems that will prevent relapses and sores while allowing free knee and ankle motion necessary to develop leg muscle strength.

SUMMARY OF INVENTION

It is an object of the present invention to provide a system and method for retaining a child's foot in an efficient manner.

It is a feature of the present invention to utilize a shoe with a sole and heel combination having an integrated attachment mechanism for connecting to a foot and ankle abduction splint (or orthosis) (AFO).

It is an advantage of the present invention to permit a child to wear a non-conspicuous and a normal use interference-free shoe which is readily attachable to an AFO splint.

It is another feature of the present invention to include a shoe having an opening at the heel which permits viewing of both sides of the heel when disposed in the shoe.

It is an advantage of the present invention to achieve improved efficiency in fully inserting a child's foot into a shoe.

It is yet another feature of the present invention to include a relatively inflexible sole section, a pliable interior foot cradling segment, and a relatively flexible shoe upper section.

It is an advantage of the present invention to provide comfort and firm support to a patient's feet.

The present invention is an apparatus and method for holding a child's feet in a predetermined therapeutic arrangement where the apparatus and method are designed to satisfy the aforementioned needs, provide the previously stated objects, include the above-listed features, and achieve the already articulated advantages. The present invention is carried out in a "discomfort-less" manner in a sense that much of the patient discomfort often associated with wearing, donning, and securing to an AFO splint, a pair of shoes, has been greatly reduced.

Accordingly, the present invention is a system and method including a shoe having a sole and heel with an integral mating mechanism for mating with an AFO splint, a comfortable pliable inner foot cradle and a comfortable shoe upper for ankle support.

BRIEF DESCRIPTION OF DRAWINGS

The invention may be more fully understood by reading the following description of the preferred embodiments of the invention, in conjunction with the appended drawings wherein.

DETAILED DESCRIPTION

Figures 1, 2:
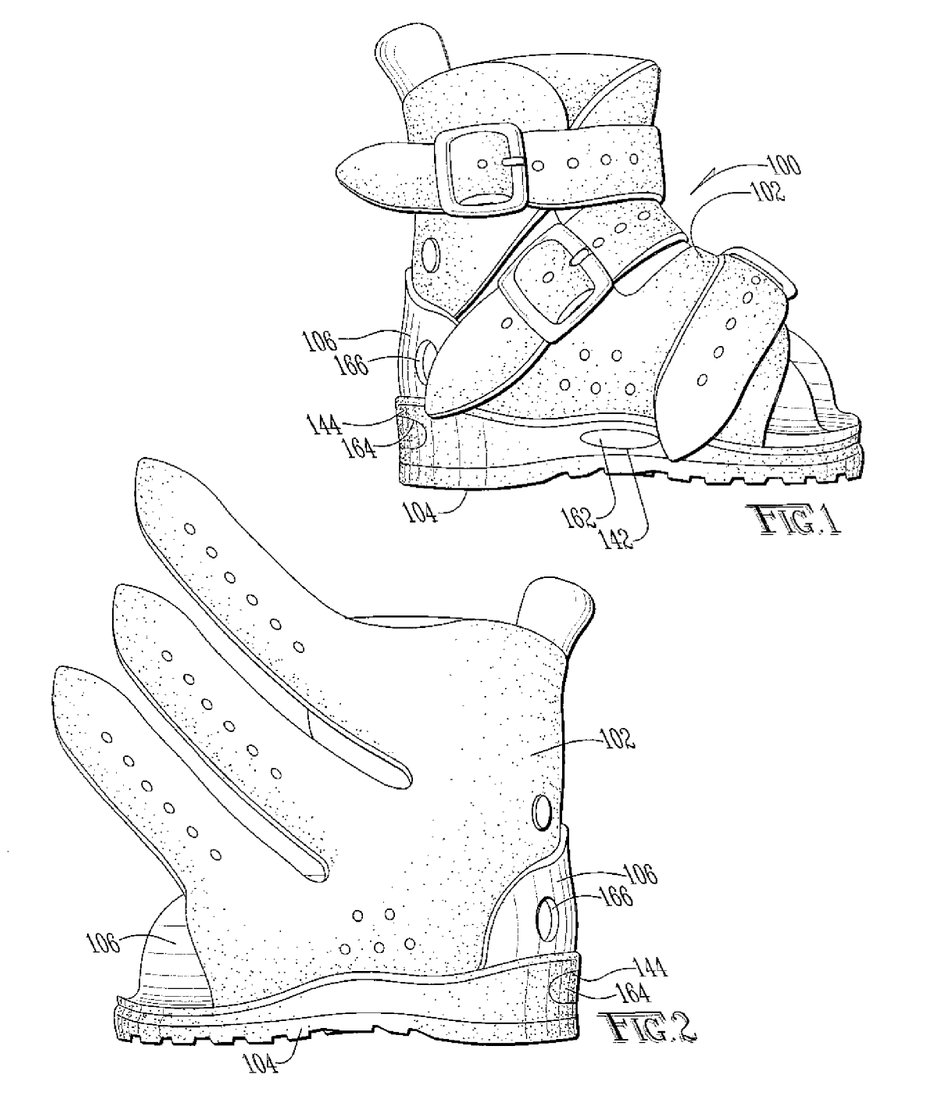
FIG. 1 is a side view of a shoe of the present invention.
FIG. 2 is a side to rear view of the shoe of FIG. 1 with the straps elevated for display purposes.

Now referring to the drawings wherein like numerals refer to like matter throughout, and more specifically referring to FIG. 1, there is shown an article of footwear 100, of the present invention. Footwear 100 is shown having a upper 102 which could be any type of material, including leather, fabric, vinyl or other material suitable for a shoe or sandal. Footwear 100 further includes a sole 104, which is preferably a single molded piece of plastic material, such as a flexible polymer. Other material suitable for shoe or sandal soles could be used as well. Also shown is insole 106, which is disposed above upper 102 and generally within upper 102.

Preferably, insole 106 is a single piece of molded polyurethane or rubber-like material. Preferably, insole 106 is pliable enough so as to permit it to conform to the shape of a child's foot when inserted therein and secured thereon by upper 102.

Insole 106 is secured to sole 104 by glue and may be supplemented, if necessary, providing an insole side protuberance 162 to extend through a sole side hole 142 in sole 104. Similarly, insole heel protuberance 164 extends through sole heel hole 144 and thereby holds insole 106 stable with respect to sole 104. Insole 106 is also shown having an insole heel right viewing hole 166, which is located near the heel of the insole 106, so that it can readily be seen that a child's foot is in contact with the insole 106. In a preferred embodiment, the insole heel right viewing hole 166 is a pair of holes on opposite sides of the heel or is a single hole which spans to both sides of the heel. In either embodiment, it would be possible to view the placement of the child's foot with respect to the insole 106 from a vantage point on either side of the heel.

Now referring to FIG. 2, there is shown an opposite side of footwear 100 of FIG. 1.

Figure 3:
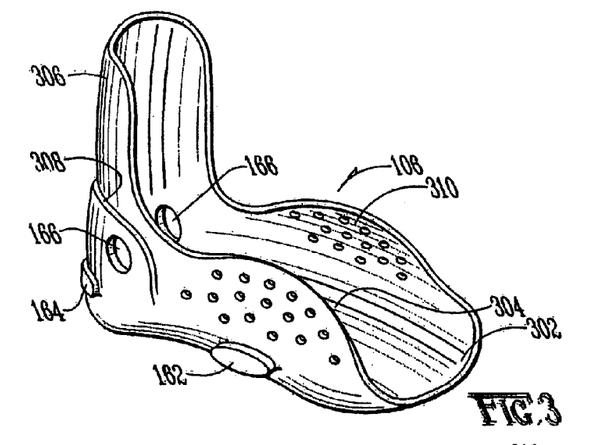
FIG. 3 is a perspective view of the in-foot cradle of FIG. 1.

Now referring to FIG. 3, there is shown a perspective view of the insole 106 of FIG. 1 when it is separated from footwear 100. Insole 106 is shown having an insole toe end 302 and an insole sole foot side 304. Preferably, insole sole foot side 304 is generally a flat surface without substantial contours to fit to an arch of a foot. Insole 106 includes an insole heel and ankle support 306 with an insole strap support 308 which keeps an ankle support strap from slipping downward. Insole 106 further includes insole side wall 310 on opposing sides of insole sole foot side 304. In a preferred embodiment, insole sole foot side 304, insole side wall 310 and insole heel and ankle support 306 all are portions of a single molded piece of urethane, pliable rubber-like material or flexible polymer material.

Figures 4, 5:
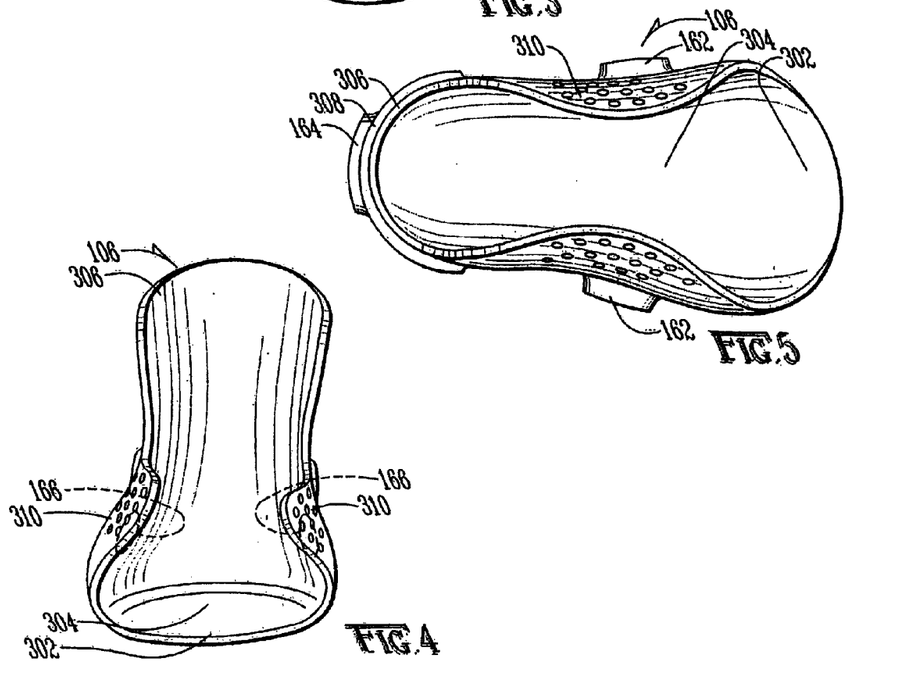
FIG. 4 is a front view of the foot cradle of FIG. 3.
FIG. 5 is a top view of the foot cradle of FIG. 4.

Now referring to FIGS. 4 and 5, there are shown front and bottom views, respectively of the insole 106 of FIGS. 1, 2 and 3.

Figure 6:
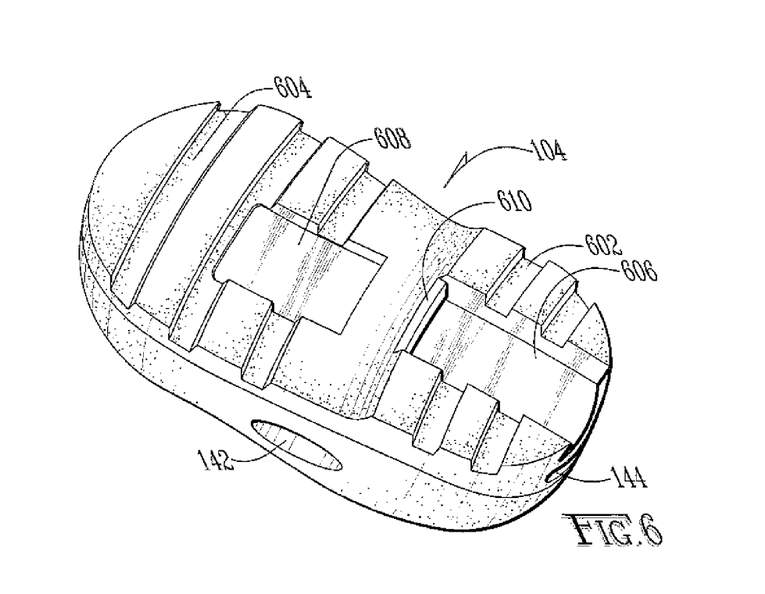
FIG. 6 is a bottom view of the sole portion of the shoe of FIG. 1.

Now referring to FIG. 6, there is shown a perspective view of the bottom of sole 104 of the footwear 100 FIG. 1. Sole heel 602 is shown disposed at an opposite end of sole 104 from sole toe end 604. Sole heel 602 has a sole attachment receiving groove 606 therein, which is separated from quick release push button receiving void 608 by quick release button barrier 610. Preferably, all of these features, sole heel 602, sole toe end 604, sole attachment receiving groove 606, quick release push button receiving void 608 and quick release button barrier 610, are integrally formed in a single piece of durable plastic or other material suitable for a rigid shoe sole. This material may need to be more rigid than a typical shoe sole material because of the need for increased lateral forces owing to the use of the splint between the shoes.

Figure 7:
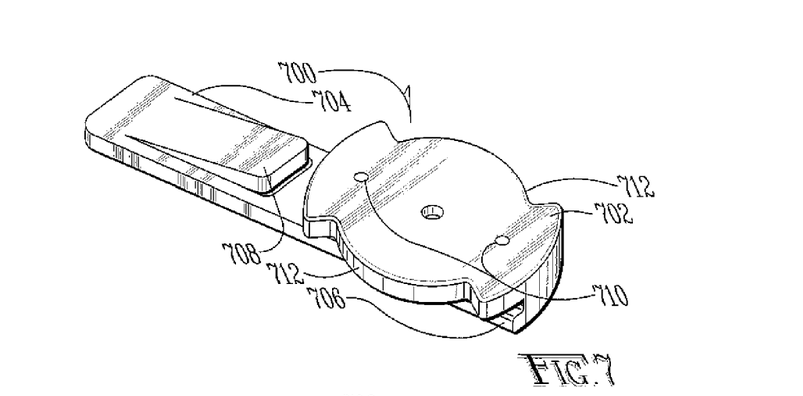
FIG. 7 is a bottom view of the clip mechanism of the present invention.
Figure 8:
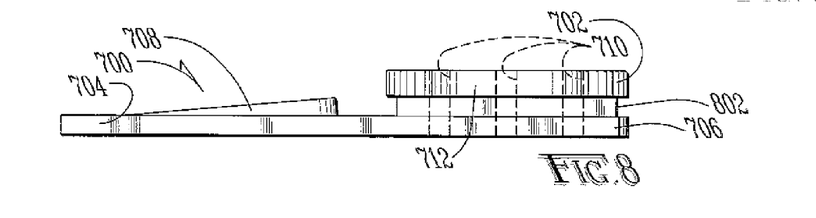
FIG. 8 is a side view of the clip mechanism of FIG. 7. in combination with an adjustment end of the bar of FIGS. 11 and 12.
Figure 14:
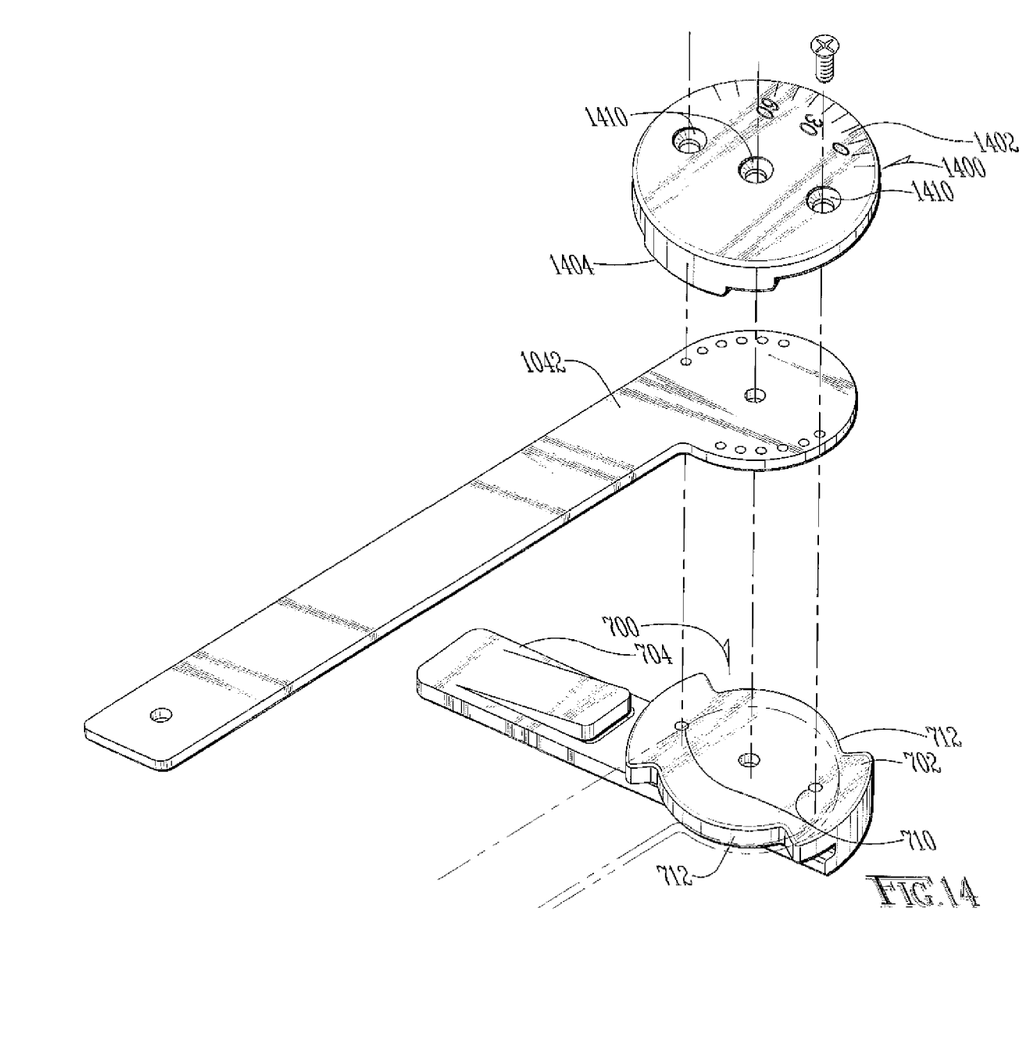
FIG. 14 is an exploded view of the angular adjustment mechanism of the present invention.

Now referring to FIG. 7, there is shown an angular adjustment/quick release member 700, which is configured to be inserted into sole attachment receiving groove 606 and quick release push button receiving void 608 of FIG. 6, by first inserting quick release front end 704 into sole attachment receiving groove 606 and sliding in further until quick release button 708 snaps into a locked position in quick release push button receiving void 608. Quick release button 708 is preferably biased outward by a spring-like structure or arrangement. Angular adjustment/quick release member 700 includes angular adjustment base 702, which is coupled to quick release back end 706 by angular adjustment/quick release riser 802 (FIG. 8). Angular adjustment base 702 has a plurality of angular adjustment fixing screw mating holes 710 therein. Angular adjustment base 702 further has a pair of angular adjustment grooves 712 therein for receiving portions of groove penetrating portion 1402 (FIG. 14).

Now referring to FIG. 8, there is shown a side view of the angular adjustment/quick release member 700 of FIG. 7.

Figures 9, 10:
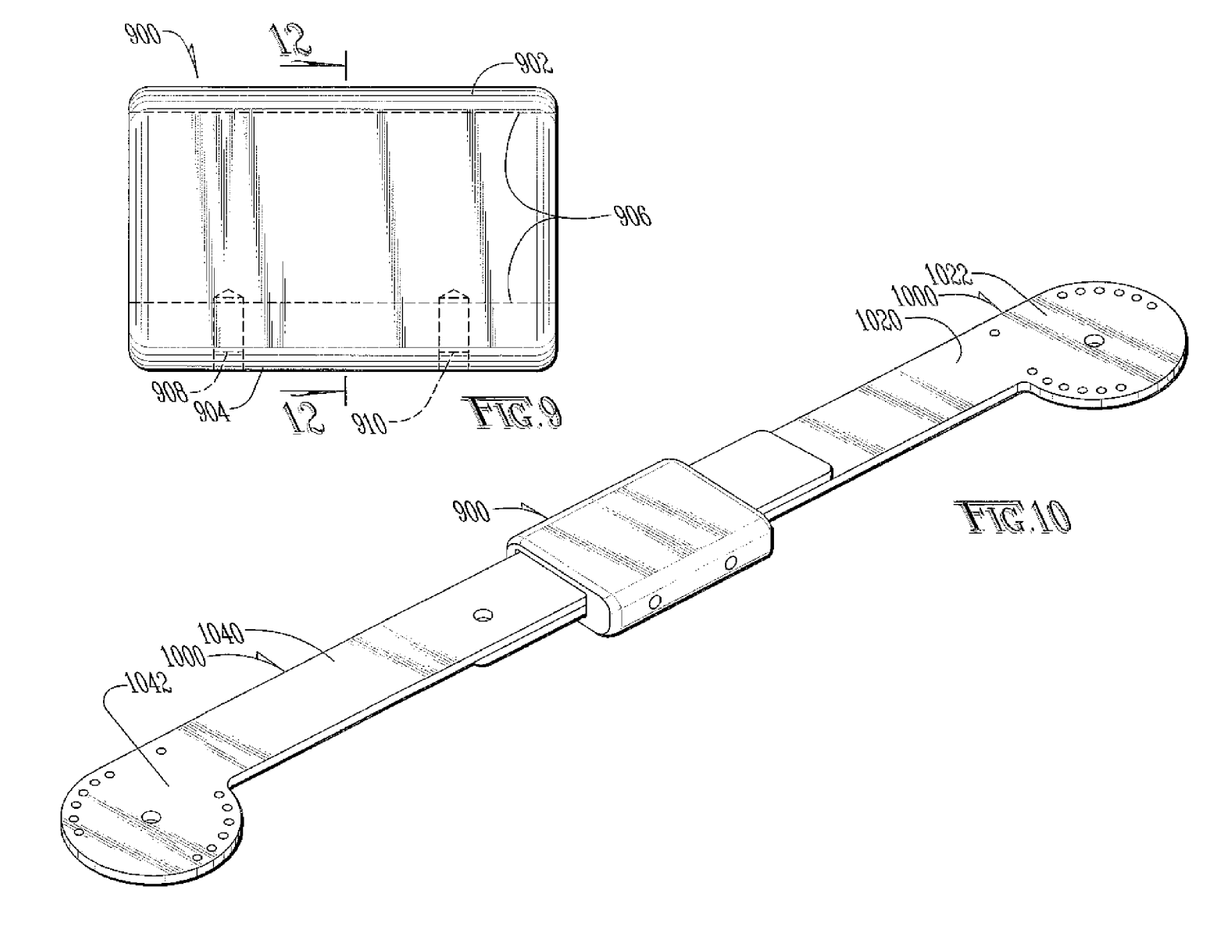
FIG. 9 is a top view of a central joining piece of the splint of FIG. 10, where the dashed lines refer to the edges of the elongated portions of the splint halves of FIG. 11.
FIG. 10 is a perspective view of a splint of the present invention, including a central joining piece of FIG. 9 and opposing splint halves of FIG. 11.
Figures 11, 12, 13:
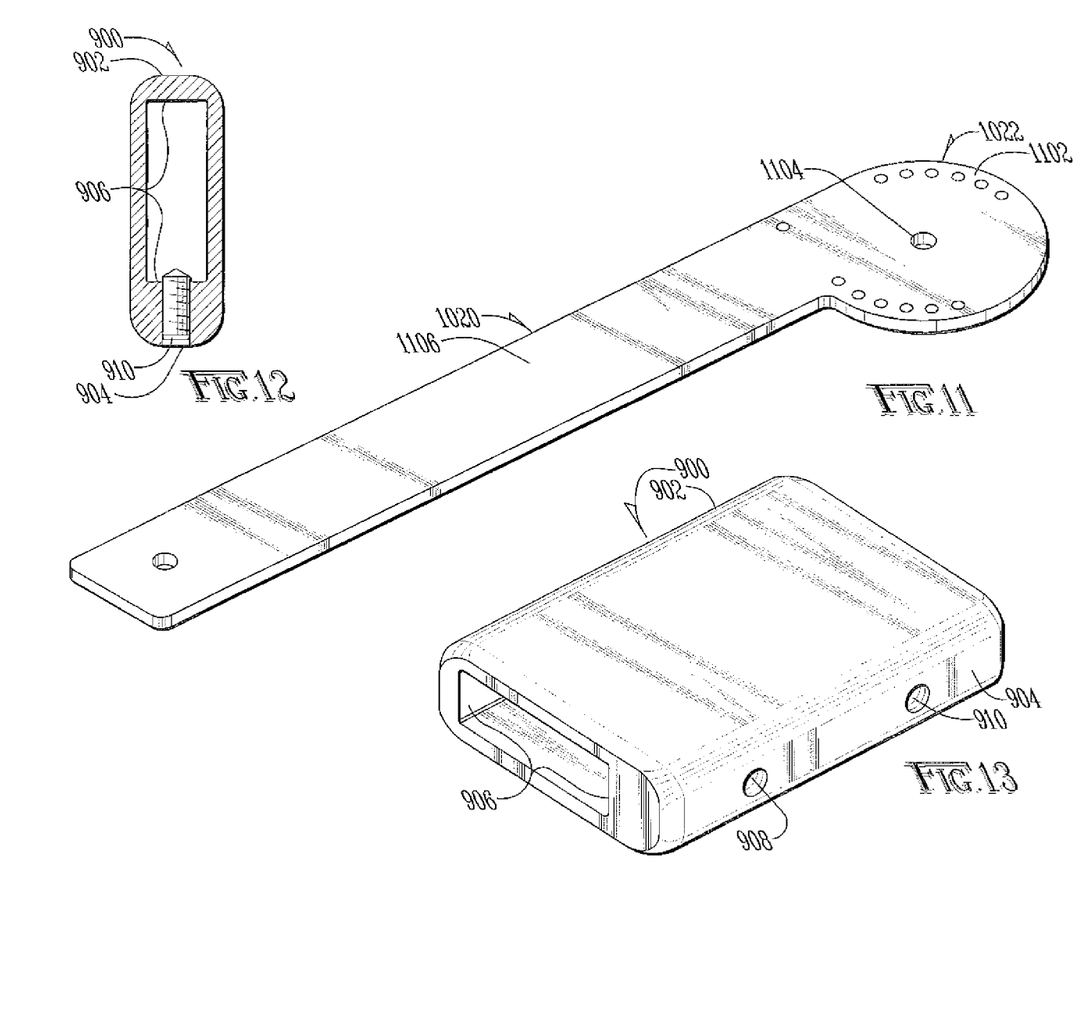
FIG. 11 is a perspective view of one of the opposing splint halves of the present invention.
FIG. 12 is a cross-sectional view of the central joining piece of FIG. 9 taken on line 12—12.
FIG. 13 is a perspective view of the central joining piece of FIG. 13.

Now referring to FIG. 9, there is a cross-section view of a shoe separation setting device 900, also shown in FIGS. 10, 12 and 13. The dashed lines show the shoe separation bar-receiving cavity edges 906. Shoe separation setting device 900 has a shoe separation setting device back side 902 and a shoe separation setting device front side 904, as well as a first set screw 908 and a second set screw 910. Preferably, shoe separation setting device 900 is made of a strong and rigid plastic material. First set screw 908 and second set screw 910 are shown extending through the shoe separation setting device front side 904 of shoe separation setting device 900. The purpose of first set screw 908 and second set screw 910 is to function as a set screw fixing the location of adjustable splint right rigid bar 1020 and adjustable splint left rigid bar 1040 (FIG. 10) at a set point. The therapeutic benefits of the Ponseti Method require that the separation of the feet be adjustable to differing fixed amounts during the treatment. The first set screw 908 and the second set screw 910 permit this adjustment. These set screws function similarly to the set screws found in the AFO or Markell Dennis Browne Splint discussed above.

Now referring to FIG. 10, there is shown an adjustable splint assembly 1000 which includes a shoe separation setting device 900, an adjustable splint right rigid bar 1020, having an adjustable splint right angular adjustment end 1022 and an adjustable splint left rigid bar 1040 having an adjustable splint left angular adjustment end 1042. Preferably, adjustable splint right rigid bar 1020 and adjustable splint left rigid bar 1040 are rigid and strong metal bars; however, other suitable materials could be used as well.

Now referring to FIG. 11, there is shown a close-up view of the adjustable splint right rigid bar 1020 of FIG. 10. Adjustable splint right rigid bar 1020 has a plurality of adjustable splint right angular adjustment end adjustment screw holes 1102 and an adjustable splint right angular adjustment end center screw hole 1104 in the adjustable splint right angular adjustment end 1022. Adjustable splint right rigid bar 1020 has a right rigid bar shank 1106, which extends into the shoe separation setting device 900 of FIG. 10. Adjustable splint right rigid bar 1020 is designed to be used with the shoe separation setting device 900.

Now referring to FIG. 12, there is shown a cross-sectional view of the shoe separation setting device 900 of FIGS. 9 and 13.

Now referring to FIG. 13, there is shown a perspective view of the shoe separation setting device 900 of FIGS. 9, 10 and 12.

Now referring to FIG. 14, there is shown an exploded view of a complete assembly of the present invention in the area around the angular adjustment section of one end of the adjustable splint assembly 1000. There is shown the angular adjustment/quick release member 700 with its angular adjustment fixing screw holes 710. Adjustable splint left angular adjustment end 1042 is then disposed on angular adjustment base 702, so that it fits inside the angular adjustment grooves 712 and that the center hole in adjustable splint left angular adjustment end 1042 aligns with the center of the angular adjustment fixing screw holes 710. Then, the adjustable splint left angular adjustment end 1042 is held in place with respect to the angular adjustment/quick release member 700 when angular adjustment guide cap 1400 is placed over the adjustable splint left angular adjustment end 1042 and the groove penetrating portion 1402 fits into one of the angular adjustment grooves 712. The rigid bar clearance riser 1404 gives space for the adjustable splint left angular adjustment end 1042 to rest on the angular adjustment base 702. The center of the angular adjustment screw holes 1410 is aligned with the center of the angular adjustment fixing screw holes 710 and the center hole in adjustable splint left angular adjustment end 1042, and a screw is inserted therein. With this arrangement, the quick release front end 704 and the adjustable splint left rigid bar 1040 are able to be moved to and locked into a series of discrete angular adjustments.

Figure 15:
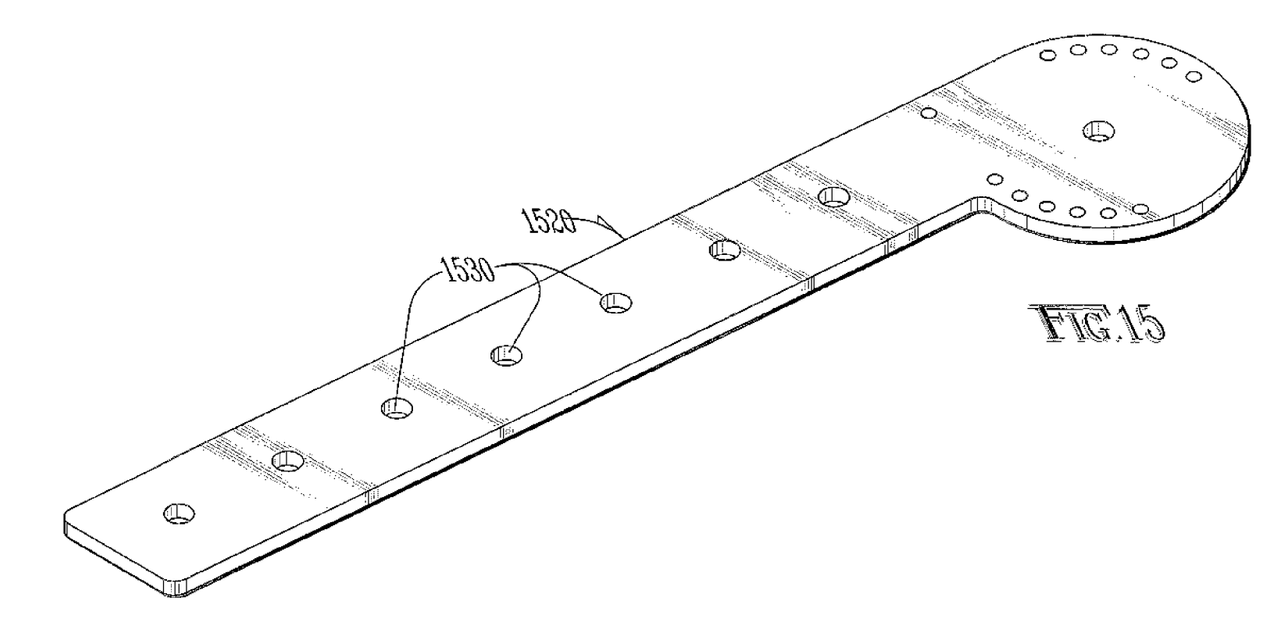
FIG. 15 is a drilled horizontal cross piece for a splint of the present invention.

Now referring to FIG. 15, there is shown a bolt through rigid bar 1520 which is similar in overall function to adjustable splint right rigid bar 1020 except that it is designed to have a bolt extend through the plurality of bolt through rigid bar bolt receiving holes 1530 therein. The bolt or bolts could perform the same function as the shoe separation setting device 900, namely, fixing the overall combined length of the two bars and, therefore, the separation distance between the patient's feet.

Figure 16:
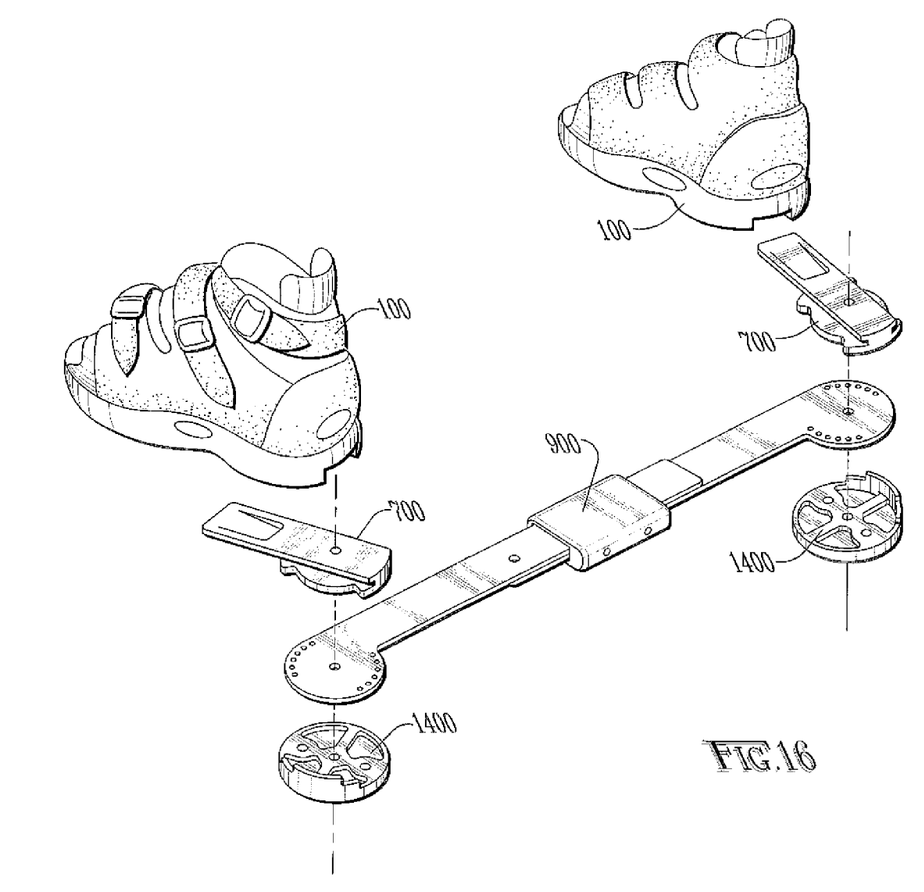
FIG. 16 is an exploded view of the foot wear, angular adjustment/quick release member and adjustable splint assembly of the present invention.

Now referring to FIG. 16, there is shown an exploded view of the present invention with two shoes coupled together.

In operation, the present invention can be used to carry out the Ponseti method of club foot treatment as follows:

Adjustable splint right rigid bar 1020 and adjustable splint left rigid bar adjustable splint left rigid bar 1040 are coupled together using a bolt or shoe separation setting device 900. The angular adjustment mechanisms on each end of the adjustable splint assembly 1000 are assembled as described with respect to FIG. 14. The angle is set by inserting a second screw through one of the adjustable splint right angular adjustment end adjustment screw holes 1102. The footwear 100 is attached to the angular adjustment/quick release member 700 by insertion of the quick release front end 704 into the sole attachment receiving groove 606 and quick release push button receiving void 608 until the quick release button 708 snaps into place beyond the quick release button barrier 610. At this point, the patient's feet can be placed in the footwear 100 and secured. Proper placement of the feet in the footwear 100 can be assured by viewing through the insole heel right viewing hole 166.

In an alternate approach, the footwear 100 can be secured to the patient's feet and then the angular adjustment/quick release member 700 is coupled to the footwear 100.

Throughout this description, reference is made to the Ponseti method and to Dennis Browne splints, because these methods and apparatuses are well known in the art and are believed to be the environment where the present invention would most likely be used. However, the novel aspects of the present invention could be used with other methods and in splints other than Dennis Browne splints.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

The invention claimed is:

1. A system for maintaining a child's feet in a predetermined therapeutic arrangement, the system comprising:
    a splint comprising:
        a rigid elongated member comprising a left end and a right end;
        a right shoe engaging plate adjustably coupled to said elongated member;
        a left shoe engaging plate adjustably coupled to said elongated member;
        a right end adjustment mechanism disposed between said right shoe engaging plate and said elongated member, said right end adjustment mechanism for making angular adjustments;
        a left end adjustment mechanism disposed between said left shoe engaging plate and said elongated member, said left end adjustment mechanism for making angular adjustments;
        a right quick release mechanism coupled to said right shoe engaging plate;
        a left quick release mechanism coupled to said left shoe engaging plate;
        a right shoe detachably coupled to said right quick release mechanism;
        a left shoe detachably coupled to said left quick release mechanism;
        a left recess disposed inside of a left sole of the left shoe, wherein said left sole is a single piece of molded material and wherein the left recess is configured to receive and selectively latch therein said left quick release mechanism;
        a right recess disposed inside of a right sole of the right shoe, wherein said right sole is a single piece of molded material and wherein said right recess is configured to receive and selectively latch therein said right quick release mechanism; and
    wherein said right shoe further comprises a foot and ankle holding removable insert which has an orifice on each side of a heel engaging section which permits viewing of a patient's foot as it is inserted into said right shoe.

2. A system of claim 1 wherein said removable insert has a first orifice outside end on one side of the heel engaging section and a second orifice outside end on an opposing side of the heel engaging section, such that viewing of a patient's foot is permitted through at least some area extending between the first orifice outside end and the second orifice outside end.

3. A system of claim 1 wherein said orifice on each side of the heel engaging section is a plurality of discrete orifices separated by material across a portion of said heel engaging section configured to surround a portion of a patient's heel.

4. A system for maintaining a child's feet in a predetermined therapeutic arrangements, the system comprising:
    a splint comprising:
        a rigid elongated member comprising a left end and a right end;
        a shoe engaging plate adjustably coupled to said elongated member at each of said left end and said right end;
        a right end adjustment mechanism disposed between said shoe engaging plate and said right end of said elongated member, said right end adjustment mechanism for making angular adjustments;
        a left end adjustment mechanism disposed between said shoe engaging plate and said left end of said elongated member, said left end adjustment mechanism for making angular adjustments;
        a shoe coupled to each of said shoe engaging plate;
        said shoe comprising a single piece removable inner foot and heel cradling insole insert, which is sized, shaped and configured to provide full heel support;

wherein said single piece inner foot and heel cradling insole insert has a relatively flat insole sole foot side and a pair of opposing insole side walls and an insole heel and ankle support section; and wherein absence of material in said insole heel and ankle support section permits visual inspection from both sides of a patient's heel placement of a patients heel into said insole heel and ankle support section and contact with said insole sole foot side, while providing support for the heel and ankle.

5. A system of claim 4 wherein said absence of material is a plurality of discrete insole heel right viewing holes disposed on opposing sides of said insole heel and ankle support section.

6. A system for maintaining a child's feet in a predetermined therapeutic arrangement, the system comprising:
   a splint comprising:
      a rigid elongated member comprising a left end and a right end;
      a shoe engaging plate adjustably coupled to said elongated member;
      a right end adjustment mechanism disposed between said shoe engaging plate and said elongated member, said right end adjustment mechanism for making angular adjustments;
      a shoe coupled to said shoe engaging plate;
      said shoe comprising a single piece inner foot cradling insole member;
   wherein said shoe engaging plate is not coupled to said shoe by a threaded elongated member;
   wherein said shoe is coupled, via a quick release mechanism, to a first end of an adjustable splint assembly;
   further comprising a second shoe coupled to a second end of said adjustable splint assembly;
   wherein said adjustable splint assembly further comprises a shoe separation setting device comprising a first set screw and a second set screw; and
   wherein said single piece inner foot cradling insole member has a plurality of protuberances which extend through holes in said sole of said shoe.

* * * * *